(12) United States Patent
Piuk et al.

(10) Patent No.: US 6,620,379 B1
(45) Date of Patent: Sep. 16, 2003

(54) APPARATUS AND METHOD OF TREATMENT OF WOUNDS, BURNS AND IMMUNE SYSTEM DISORDERS

(75) Inventors: Vladimir Piuk, Kiryat Yam (IL); Mark Schnaiderman, Kiryat Yam (IL); Nelly Mizruchin, Kiryat Yam (IL)

(73) Assignee: S.P.M. Recovery Ltd., Ramat-gan (IL)

( * ) Notice: Subject to any disclaimer, the term of this patent is extended or adjusted under 35 U.S.C. 154(b) by 0 days.

(21) Appl. No.: 09/467,933

(22) Filed: Dec. 21, 1999

Related U.S. Application Data

(63) Continuation-in-part of application No. 09/057,790, filed on Apr. 9, 1998, now Pat. No. 6,060,020.

(51) Int. Cl.⁷ .......................... A61L 2/20; A61M 37/00
(52) U.S. Cl. .......................... 422/3; 422/33; 422/292; 604/25
(58) Field of Search .................. 422/33, 292, 3; 73/49.3; 604/25

(56) References Cited

U.S. PATENT DOCUMENTS

| | | |
|---|---|---|
| 2,745,407 A | 5/1956 | Mueller |
| 3,907,389 A | 9/1975 | Cox et al. ............... 312/1 |
| 5,052,382 A | 10/1991 | Wainwright |
| 5,098,415 A | 3/1992 | Levin |
| 5,259,895 A | 11/1993 | Sharp |
| 5,334,355 A | 8/1994 | Faddis ................ 422/122 |
| 5,868,999 A | 2/1999 | Karlson ................ 422/30 |
| 5,932,172 A | 8/1999 | Winks ................. 422/32 |
| 5,951,948 A | 9/1999 | Duroselle et al. ......... 422/33 |

*Primary Examiner*—Elizabeth McKane
(74) *Attorney, Agent, or Firm*—Rashida A. Karmali

(57) ABSTRACT

A device for the treatment of objects using an effective amount of ozone, the device comprising at least two sealed treatment chambers into which a person inserts at least one object to be treated, each treatment chamber being hermetically sealed by a sealing means to provide a complete seal, a distribution means for delivering the ozone-oxygen to each of the treatment chambers, a control system being designed to produce a static mode operation wherein there is no ozone flow into or out of the treatment chamber except during testing periods when a negative pressure is produced in each treatment chamber. The inventions also pertains to an improved device for treating wound, ulcers, burns, skin and immune system disorders, thrombotic diseases, and disorders of blood platelets, diabetes or peripheral vascular diseases.

25 Claims, 19 Drawing Sheets

Fig.1 Block diagram of apparatus for treating objects with ozone

Fig.2 Diagram of ozone treatment

T1-sealing, T2-filling of treatment chamber, T3-ozone treatment, T4-ozone destruction
Cg/m3- ozone concentration in treatment chamber

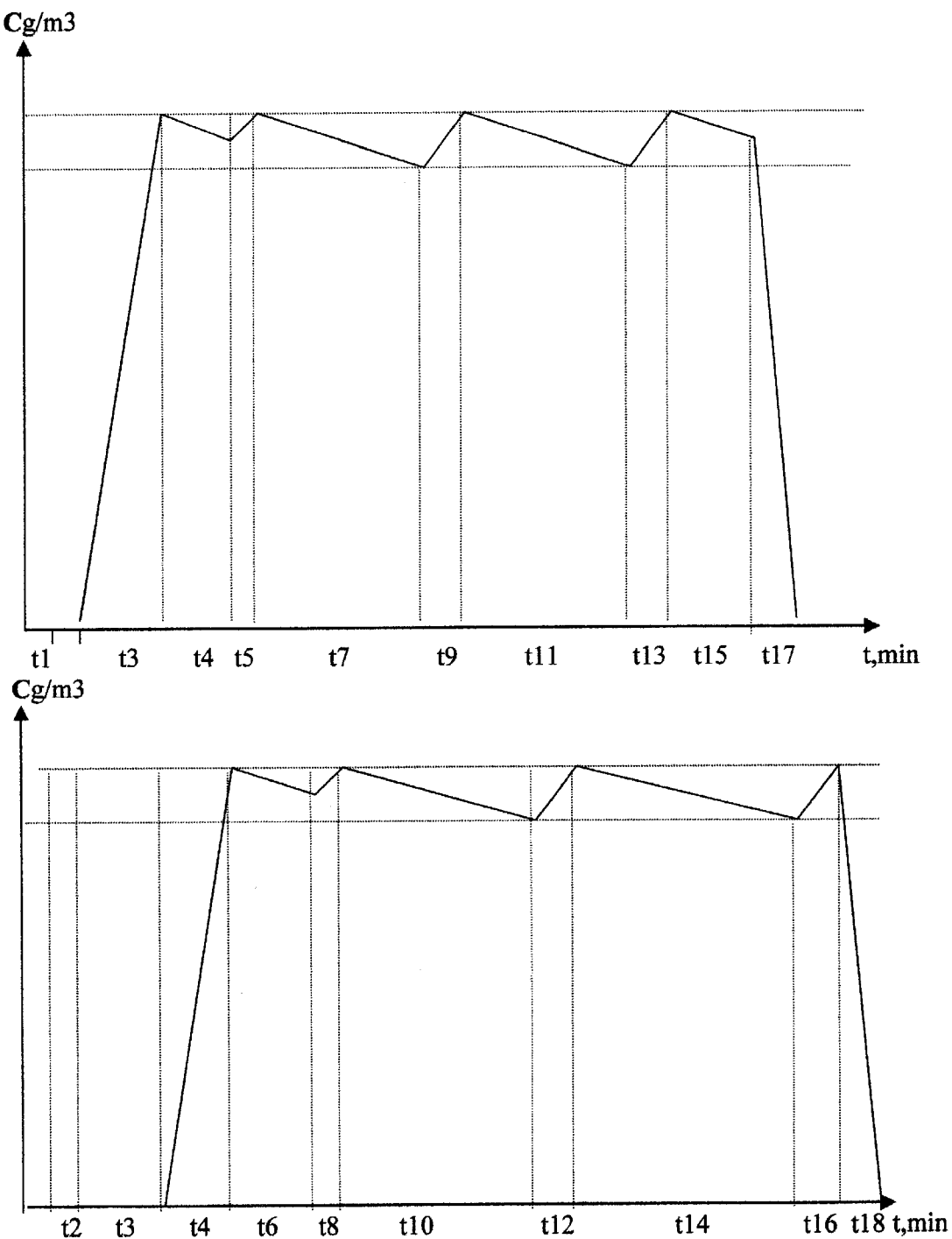
Fig.5 Diagram of ozone treatment for two chambers in Static mode operation Fig. 7 Application 1 – diabetic wound
Before ozone treatment
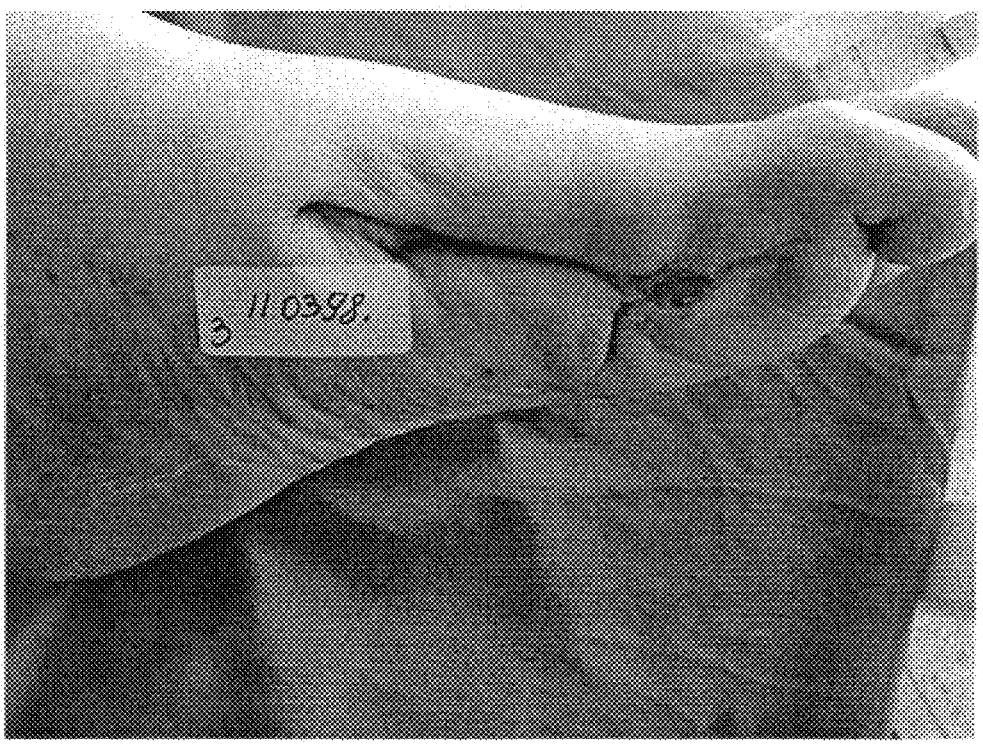
After 22 sessions of ozone treatment Fig. 8 Application 2 – Chronic venous ulcer
Before ozone treatment
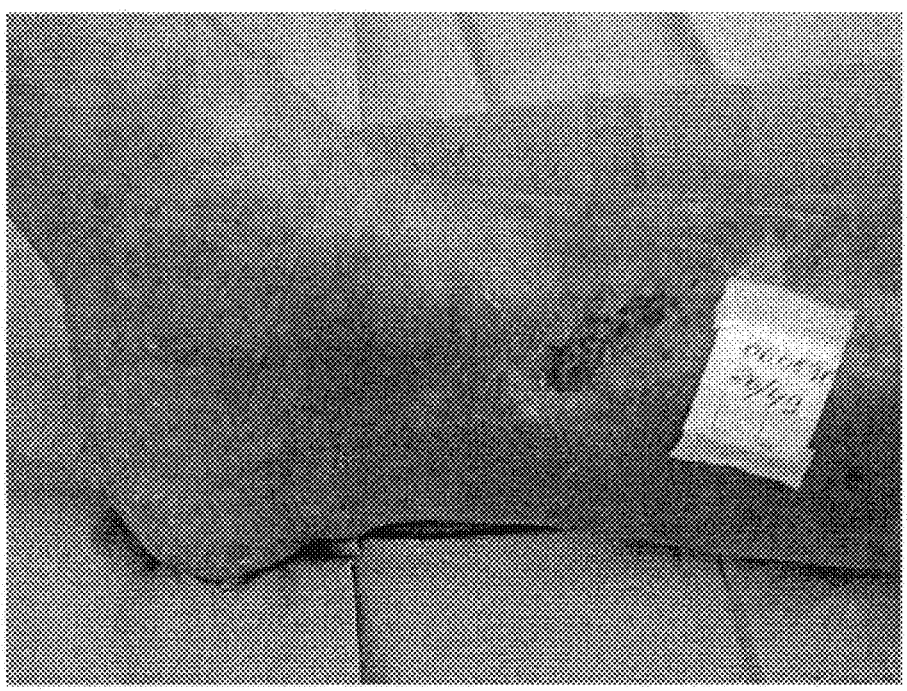
After 49 sessions of ozone treatment Fig. 9 Application 3 – Postoperation wound ( by-pass )
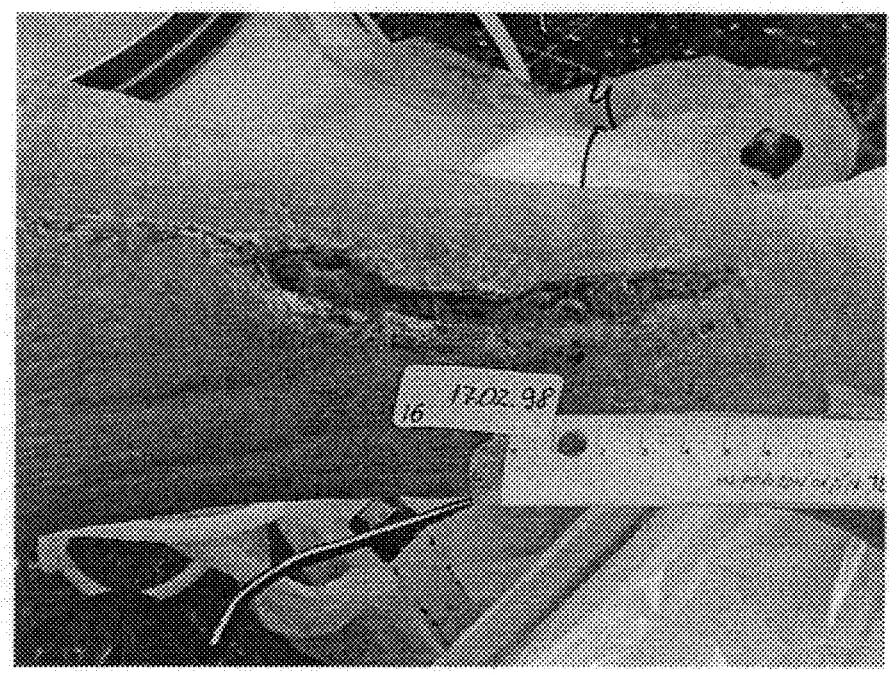
Before ozone treatment
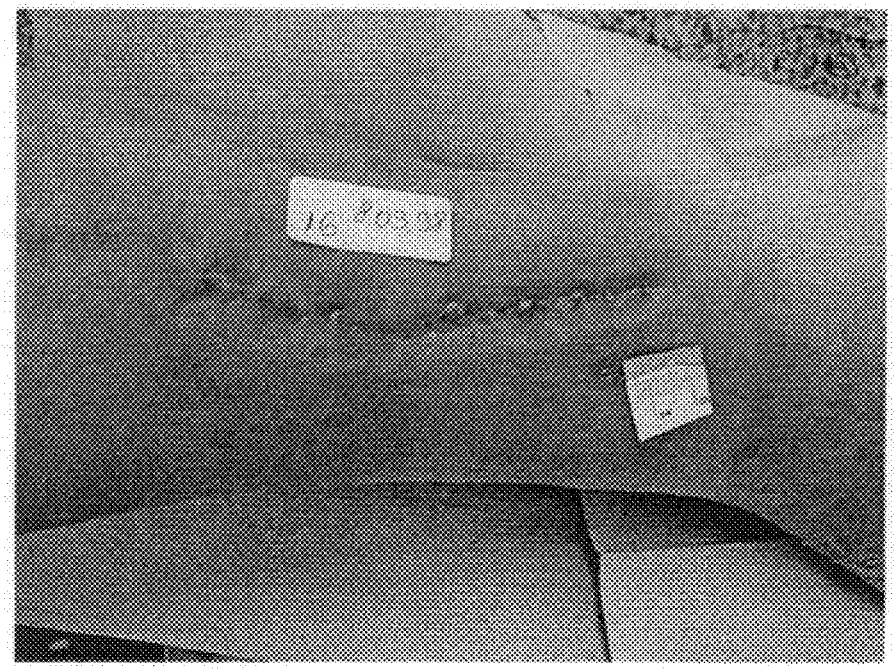
After 16 sessions of ozone treatment Fig. 10 Application 4 – Traumatic wound
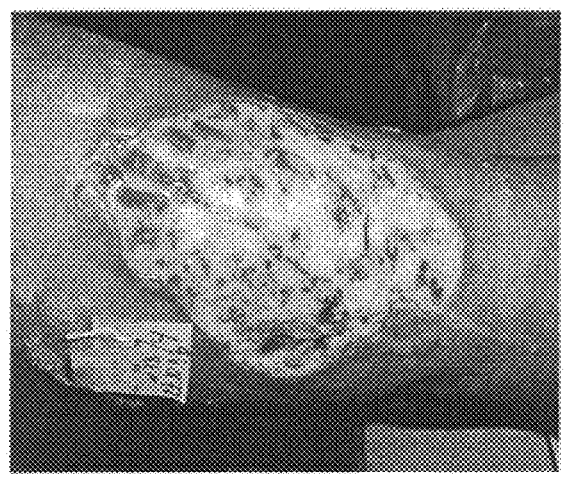
Before ozone treatment
After 26 sessions of ozone treatment ( ready for skin graft )
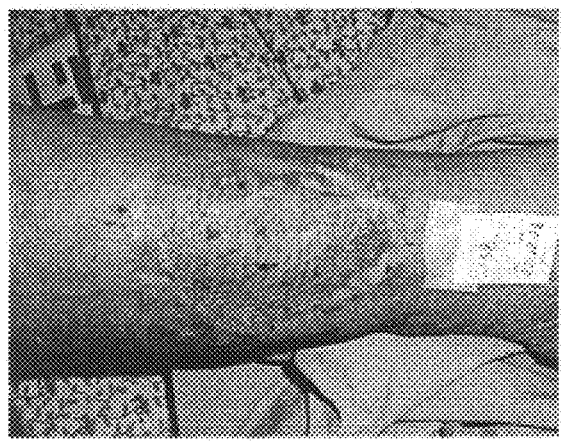
After skin graft

APPARATUS AND METHOD OF TREATMENT OF WOUNDS, BURNS AND IMMUNE SYSTEM DISORDERS

CROSS-REFERENCE TO RELATED APPLICATIONS

This Application is a Continuation-In-Part of U.S. patent application Ser. No. 09/057,790, filed Apr. 9, 1998 and now U.S. Pat. No. 6,060,020, the entire disclosure of which is incorporated herein by reference.

BACKGROUND OF THE INVENTION

The present invention is related to an improved device for treating wounds, ulcers and burns in humans, as well as to a method of treating human disease conditions associated with the skin, immune system disorders, burns, thrombotic diseases, disorders of blood platelets, diabetes and peripheral vascular diseases. The invention also pertains to provide a safe ozone treatment device for administering ozone treatments to both animate and inanimate objects in an efficient and safe manner to one or more subjects simultaneously with a device.

DESCRIPTION OF PRIOR ART

Ozone is used for sterilizing both inanimate objects including, but not limited to, water supplies, food products, surgical supplies and the like, as well as animates objects such as body parts of animals and humans for the promotion of healing. The therapeutic benefits of using ozone gas ($O_3$) or a solution thereof have been previously disclosed. These treatments rely on the oxidative characteristic of ozone which acts as a bactericide, antiviral, fungicide or germicide to destroy a wide variety of deleterious organisms. For example, U.S. Pat. No. 2,745,407 issued to Mueller et al., discloses an ozone device used to treat the human body with ozone at its orifices, for example, for nasal, ear and other orifice infections. U.S. Pat. No. 5,052,382 issued to Wainwright, discloses an ozone apparatus used to purify water, milk, biologically active fluid or wine. U.S. Pat. No. 5,098,415 issued to Levin, discloses a device for using an aqueous solution containing ozone to treat foot diseases. These devices are very limited in scope due to the fact that the treatment area is small and well defined, precluding the use of the device to affect larger body parts and/or surfaces, or for checking against ozone leakage into the atmosphere as a health hazard.

Moreover, ozone is a dangerous material and can raise a serious health hazard if not handled properly. A quantity of as little as 0.01 parts per million (ppm) of ozone in the atmosphere can be se by human beings, and a concentration of greater than 0.1 ppm is regarded as being extremely dangerous. Since ozone treatment frequently involves concentrations as high as 50,000 ppm, the consequence of even the smallest leak of ozone to the atmosphere, would be serious for anyone exposed.

Accordingly, a need exists for devices and methods for applying ozone to treat various diseases using hermetically sealed treatment chambers which would prevent or minimize the likelihood of ozone leakage to the surrounding.

Diseases and conditions which may be controlled or eradicated by having the affected part exposed to ozone include, but are not limited to diabetic lesions on the feet, fingal infections of the skin, toenails, toenail roots, athlete's foot, trichophyton rubrum, T. mentagrophytes, radiation wounds, pressure sores, decubitis, ulcers, sores, wounds, skin infections, Epidermphyton floccosum, burns, thrombotic diseases, disorders of blood platelet aggregation, disorders of the immune system, psoriasis, acne, eczema or peripheral vascular diseases.

SUMMARY OF THE INVENTION

It is therefore an object of the present invention to provide devices for ozone treatment that substantially reduce the problems associated with ozone gas leakage and thus reduce any health hazard or risk with uncontrolled ozone exposure. Another object of the invention is to provide a device for ozone treatment to both animate and inanimate objects, and to more than one subject at any time.

It is another object of the present invention to provide a method for treating an object, such method comprising introducing the object and ozone into a hermetically sealed treatment chamber to prevent ozone from leaking from the treatment chamber into the atmosphere or surrounding and to provide an indication of the seal, by a sealing means, during the course of the ozone treatment.

It is yet another object of the invention to provide a method of applying ozone to an object, the steps of which include introducing the object and a fluid mixture of ozone into the treatment chamber, treating the object in the treatment chamber in a static mode operation under conditions in which there is no flow of ozone into or out of the treatment chamber. During this static mode operation, tests are performed at specific testing periods wherein, for each test, an outflow from the chamber is produced. This outflow is tested for any drop in ozone content and further ozone is introduced into the chamber to maintain the level of ozone content therein.

It is another object of the present invention to introduce more than one object into the treatment chamber with ozone, maintain the static mode operation and provide an effective amount of ozone treatment.

It is yet another object of the present invention to provide a method for ozone treatment using a device comprising one or more sealed treatment chambers for receiving the objects. Each treatment chamber includes an inlet for introducing an ozone-oxygen mixture into the chamber, and an outlet for removing the ozone mixture therefrom. The device further includes a supply of oxygen-oxygen mixture connected to the inlet of the treatment chamber. A suction pump is connected to the outlet of the treatment chamber to produce a subatmospheric pressure or negative pressure in the chamber. Included also are the following: a distribution means for delivering the ozone-oxygen mixture to each treatment chamber, a control system for controlling the ozone-oxygen supply, a suction pump and a distribution means. The distribution means provides a check of the sealing of the chambers to ensure that no ozone leakage to the atmosphere occurs and to produce a static mode operation. During the static mode operation there is no ozone-oxygen flow into or out of the treatment chamber except during specific testing periods during which a flow with low negative pressure, lower than atmospheric pressure, is produced through the treatment chamber.

It is yet another object of the present invention to provide a device for treating an object or objects with ozone, the device comprising one or more air impermeable housing of a hollow construction to define treatment chambers each with an opening, each housing further comprising a sealing means including a flexible air-impermeable sleeve having a first end lining the opening and the opposite end extending externally to the treatment chamber and a clamping ring clamping the first end of the sleeve to the housing.

The present invention is directed to a method for wound healing which involves treatment with ozone, in animals and human beings in different conditions including, but not limited to diabetic lesions, skin disorders, bums, immune system disorders, thrombotic diseases, disorders of blood platelet aggregation, peripheral vascular diseases, fungal infections, toenail roots, athlete's foot, radiation wounds, pressure sores, ulcers, sores, psoriasis, acne, eczema or decubitis. Accordingly, an effective amount of ozone is administered in a hermetically sealed treatment chamber to an animal or individual in need thereof.

The present invention is also directed to a method of enhancing the immune system using ozone treatment.

The present invention is also directed towards inhibiting platelet aggregation with ozone treatment, thereby providing an alternate antiplatelet therapy.

The present invention is also directed towards treatment of various human diseases with ozone treatment through the oxidative action of ozone which acts as a bactericide, antiviral, fungicide or germicide to destroy a wide variety of deleterious organisms.

Still other objects and advantages of the invention will in part be obvious and will in part be apparent from the specification and working examples described herein.

4. BRIEF DESCRIPTION OF DRAWINGS

For a fuller understanding of the invention, reference is made to the following description taken in connection with the accompanying drawings, in which:

FIG. 5 illustrates a diagram of an apparatus having two chambers for ozone treatment in a Static mode operation according to the present invention;

Figure 1:
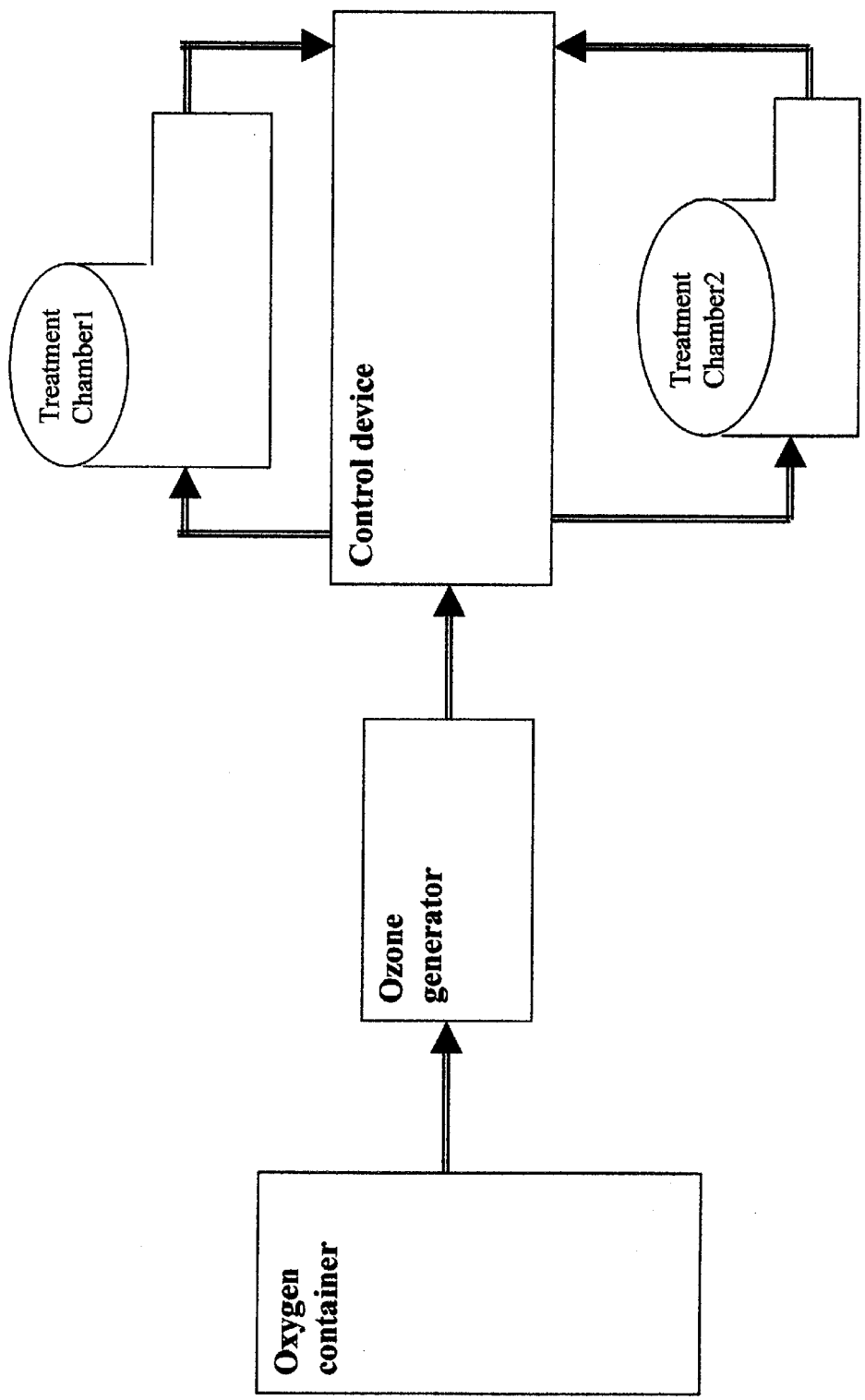
FIG. 1 illustrates a block diagram of the apparatus for treating objects with ozone.

FIG. 7 describes a diabetic wound preozone treatment and after twenty-two (22) sessions of ozone treatment in a human subject;

FIG. 8 describes a chronic venous ulcer preozone treatment and after forty-nine (49) sessions of ozone treatment in a human subject;

FIG. 9 describes a postoperative wound preozone treatment and after sixteen (16) sessions of ozone treatment in a human subject; and FIG. 10 describes a traumatic wound preozone treatment after twenty-six (26) sessions of ozone treatment and after a skin graft treatment.

5. DETAILED DESCRIPTION OF THE INVENTION

The present invention relates to an apparatus for treating objects with ozone. Ozone has been used for treating both inanimate objects, such as water supplies, food products, and the like, e.g., for sterilization purposes, as well as animate objects, such as body parts of animals or of human beings for the promotion of healing. The beneficial effects of treatment with ozone in promoting healing are now well recognized. Ozone, however, is a dangerous material and can raise a serious health hazard if not handled properly. Thus, a quantity of as little as 0.01 ppm (parts per million) of ozone in the atmosphere can be sensed by human beings, and a concentration of greater than 0.1 ppm is regarded as being extremely dangerous. When it is appreciated that ozone treatment processes frequently involve concentrations of as high 50,000 ppm, it will be seen that the smallest leak of ozone to the atmosphere can create a very real health danger to anyone in the immediate vicinity.

An object of the present invention is to provide an ozone treatment apparatus, substantially reducing the health hazard present with ozone treatments. Another object of the invention is to provide an apparatus which may be used for administering ozone treatments to both animate and inanimate objects in an efficient and effective manner, for example, to treat simultaneously more than one patient with one apparatus.

According to one aspect of the present invention, there is provided a system for treating an object with ozone comprising the steps of introducing the object to be treated and ozone into a sealed treatment chamber; checking of the chamber sealing before beginning of ozone treatment and applying a negative pressure to the treatment chamber to prevent ozone leaking from the treatment chamber into the atmosphere and to provide an indication of the condition of the seal during ozone treatment. According to another aspect of the invention, there is provided a method of treating an object with ozone comprising, introducing the object to be treated, and a fluid mixture including ozone, into a treatment chamber; and treating the object in the treatment chamber in a Static mode operation under conditions in which there is no flow of ozone into or out of the chamber except that tests are performed at testing periods, wherein, for each test, an outflow from the chamber is produced, the outflow is tested for any drop in ozone content, and a quantity of fresh ozone is introduced into the chamber to makeup for any drop of ozone content therein.

Because of Static mode operation it is possible to treat some objects simultaneously without increase of ozone generator production and equipment quantity and thus to provide a high efficiency of ozone treatment.

According to a further aspect of the invention, there is provided an apparatus or system for treating an object with ozone, comprising: one or more of the sealed treatment chambers for receiving the objects, each treatment chamber including an inlet for introducing an ozone-oxygen mixture therein, and an outlet for removing the ozone mixture therefrom; a supply of ozone-oxygen mixture connected to the inlet of the treatment chamber; a suction pump connected to the outlet of the treatment chamber to produce a subatmospheric (negative) pressure in the chamber; a distributing means for delivering of ozone-oxygen mixture to each of the treatment chambers; and a control system for controlling the ozone-oxygen supply, the suction pump and the distributing means to provide a check of chamber sealing for prevention of ozone leakage to the atmosphere and to produce a Static mode operation, wherein there is no ozone-oxygen flow into or out of the treatment chamber except short testing periods, wherein a flow with low negative pressure (lower than atmospheric) is produced through the treatment chamber.

According to a yet further aspect of the invention, there is provided an apparatus for treating an object with ozone, comprising: an air-impermeable housing of a hollow construction to define a treatment chamber, the housing being formed with an inlet and outlet for ozone, and with an opening for introducing the object to be treated into the treatment chamber; a flexible air-impermeable sleeve having one end lining the opening and the opposite end extending externally of the treatment chamber; and a clamping ring clamping the one end of the sleeve to the housing.

As will be described more particularly below, the apparatus of the present invention may be used for administering ozone treatments in a manner which substantially reduces or eliminates the health hazard presented by even extremely low concentrations of ozone in the air. In addition, the apparatus of the present invention can be used for administering ozone in an efficient and effective manner.

5.1 The Structure and Operation of the Device Simultaneous Treatment of Objects With Ozone The preferred embodiment of the invention described in FIG. 1 is for administering an ozone treatment to a body part, such as a person's foot, in order to promote healing. The apparatus illustrated in FIG. 1 includes a sealed treatment chamber for receiving the object (person's foot) to be treated; an oxygen container which is filled with compressed oxygen to deliver oxygen flow with a constant rate and pressure to the ozone generator; an ozone generator to generate an ozone-oxygen gas mixture with a preset ozone concentration at its outlet when oxygen is supplied at its inlet; and a control device for supplying the ozone-oxygen mixture to the treatment chamber with preset parameters and for controlling and maintaining these parameters with a constant value. The control device also provides a suction pump for receiving the ozone-oxygen mixture from the treatment chamber and the destruct or for destruction of ozone (reverse transforming to oxygen).

Figure 2:
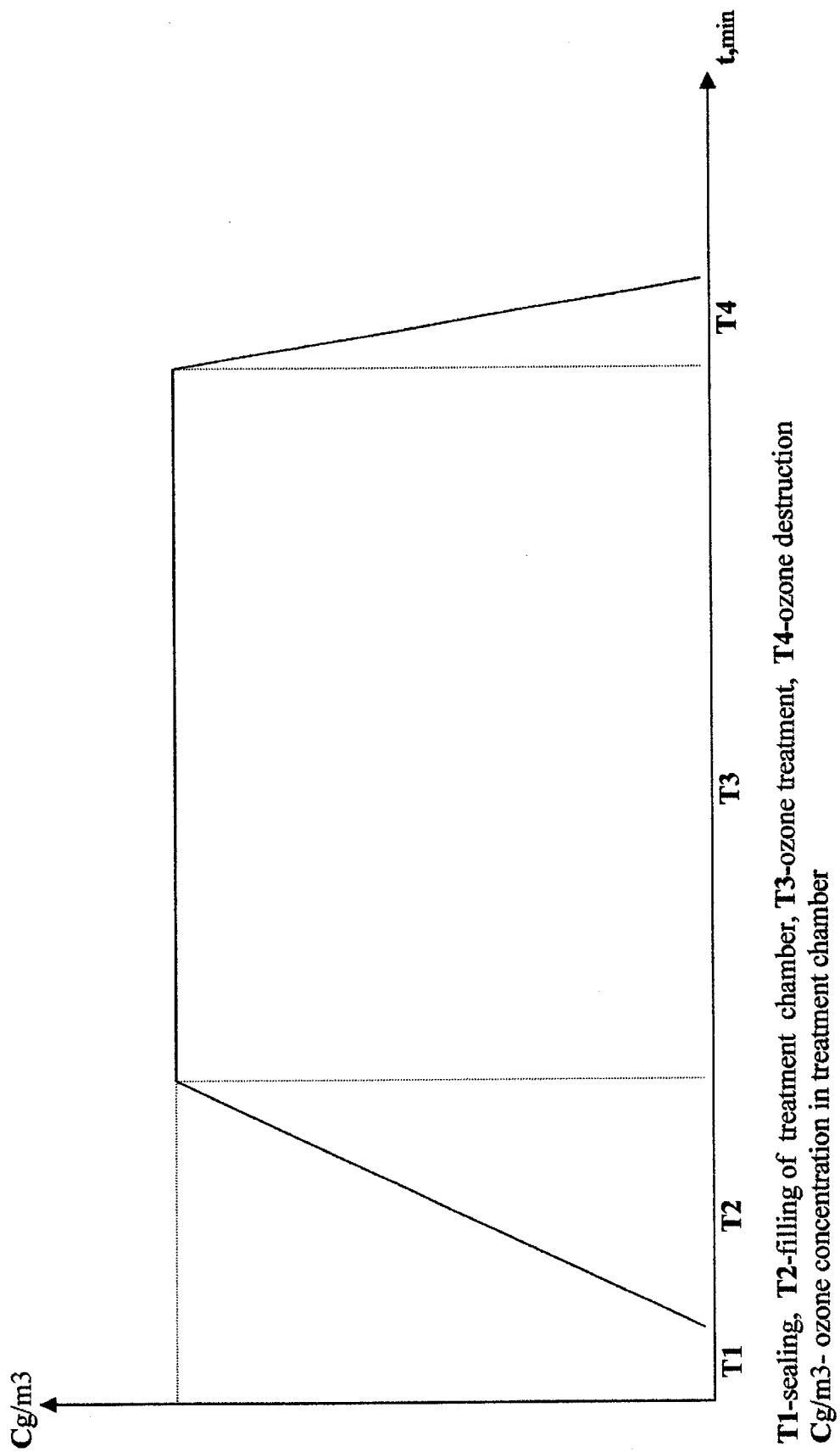
FIG. 2 illustrates the overall diagram of ozone treatment with an apparatus constructed in accordance with the present invention.

FIG. 2 illustrates the overall diagram of ozone treatment. According to FIG. 2 there are four stages of the ozone treatment, including: stage 1 (T1)—for checking of the sealing quality of the treatment chamber before delivering ozone to the treatment chamber; stage 2 (T2)—for filling of the treatment chamber with ozone until the ozone concentration within the treatment chamber is equal to the required value; stage 3 (T3)—application of proper ozone treatment at a predetermined ozone concentration and for a predetermined time; and stage 4 (T4)—for rapid destruction of ozone during a short time by delivering pure oxygen to the treatment chamber.

Figure 3:
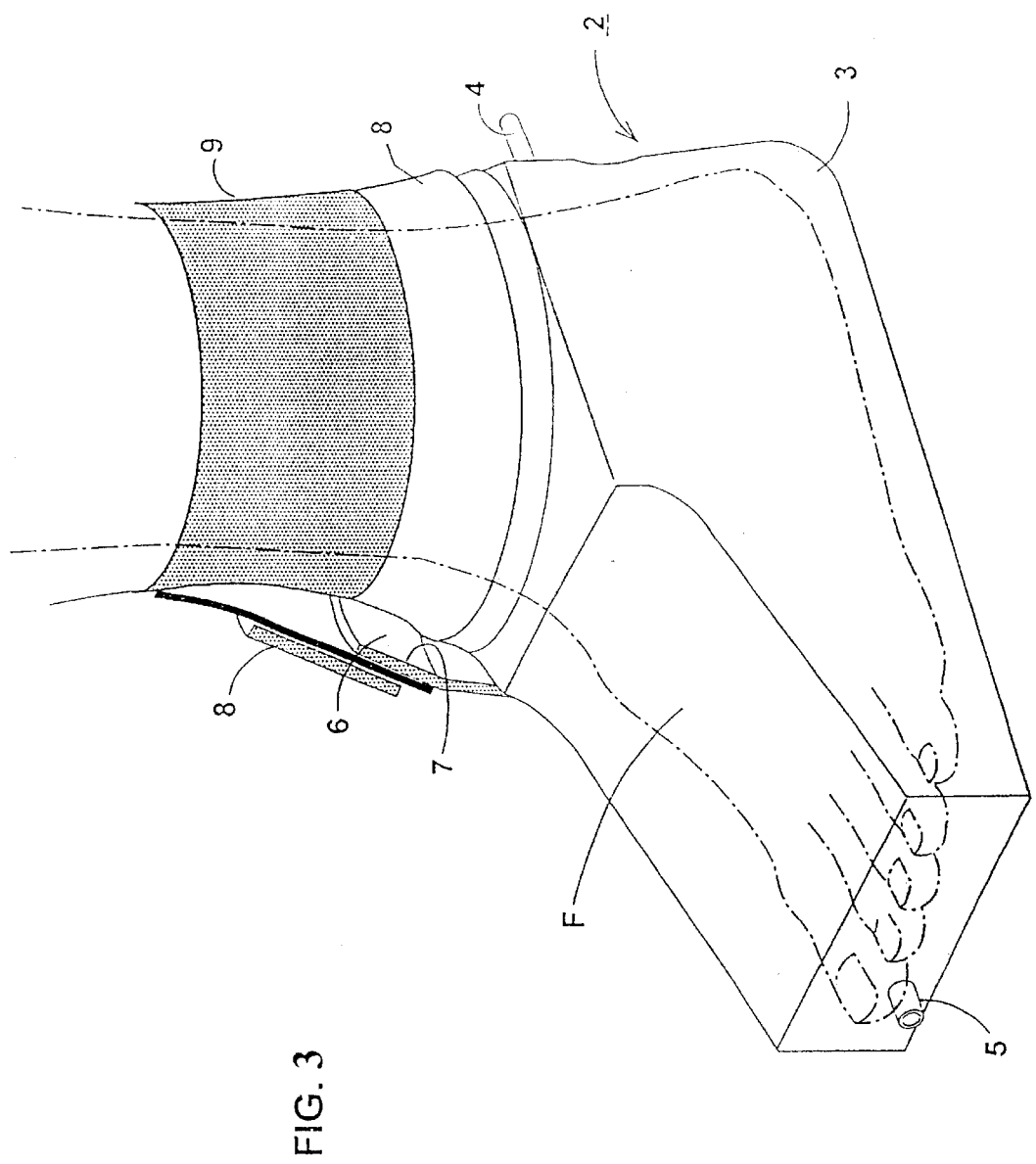
FIG. 3 illustrates one embodiment of a treatment chamber constructed in accordance with the present invention, for use in a system to treat an object with ozone.

The apparatus illustrated in FIG. 3, comprises a rigid air-impermeable housing 2 of a hollow construction to define the treatment chamber 3 within it and of a configuration which is suitable to receive the object or the foot F to be treated. Treatment chamber 3 includes an inlet 4 at one end for introducing the ozone, and an outlet 5 at the opposite end for removing the ozone. As described below, the ozone is in the form of a mixture with oxygen. Preferably, the mixture includes 95–98% oxygen and about 2–5% ozone.

Housing 2 further comprises an enlarged opening 6 for receiving the foot F to be treated. Opening 6 is circumscribed by an annular collar 7 having an outer surface of conical configuration complementary to the conical configuration of the inner surface of a locking ring 8. One end of a flexible, air-impermeable sleeve 9 is interposed between collar 7 and a clamping ring 8 and is clamped in place by a pressing collar 8 downwardly to produce a friction fit with collar 7. The opposite end of sleeve 9 extends outwardly of housing 2.

Preferably, sleeve 9 comprises an elastic material so that the outer end of the sleeve firmly grips the ankle of the person's foot to be treated, thereby providing a hermetic seal with respect to the treatment chamber 3 within housing 2. Alternatively, sleeve 9 may be of a pliable plastic material, in which case the external end of the sleeve is firmly clamped against the subject's ankle by the application of another clamping ring or band (not shown).

Figure 4:
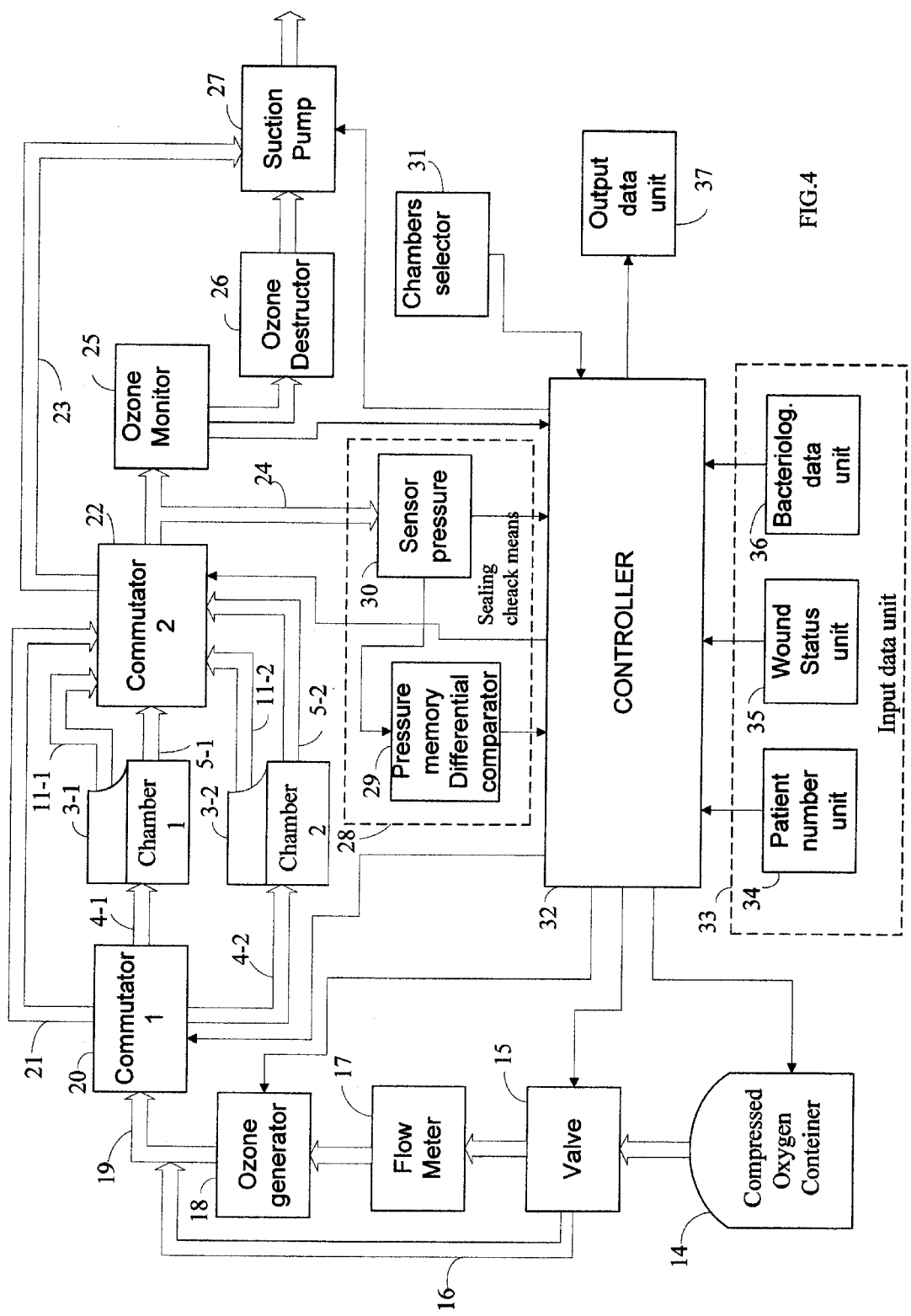
FIG. 4 illustrates in detail, a block diagram of an apparatus used for treating objects with ozone.
Figure 6A:
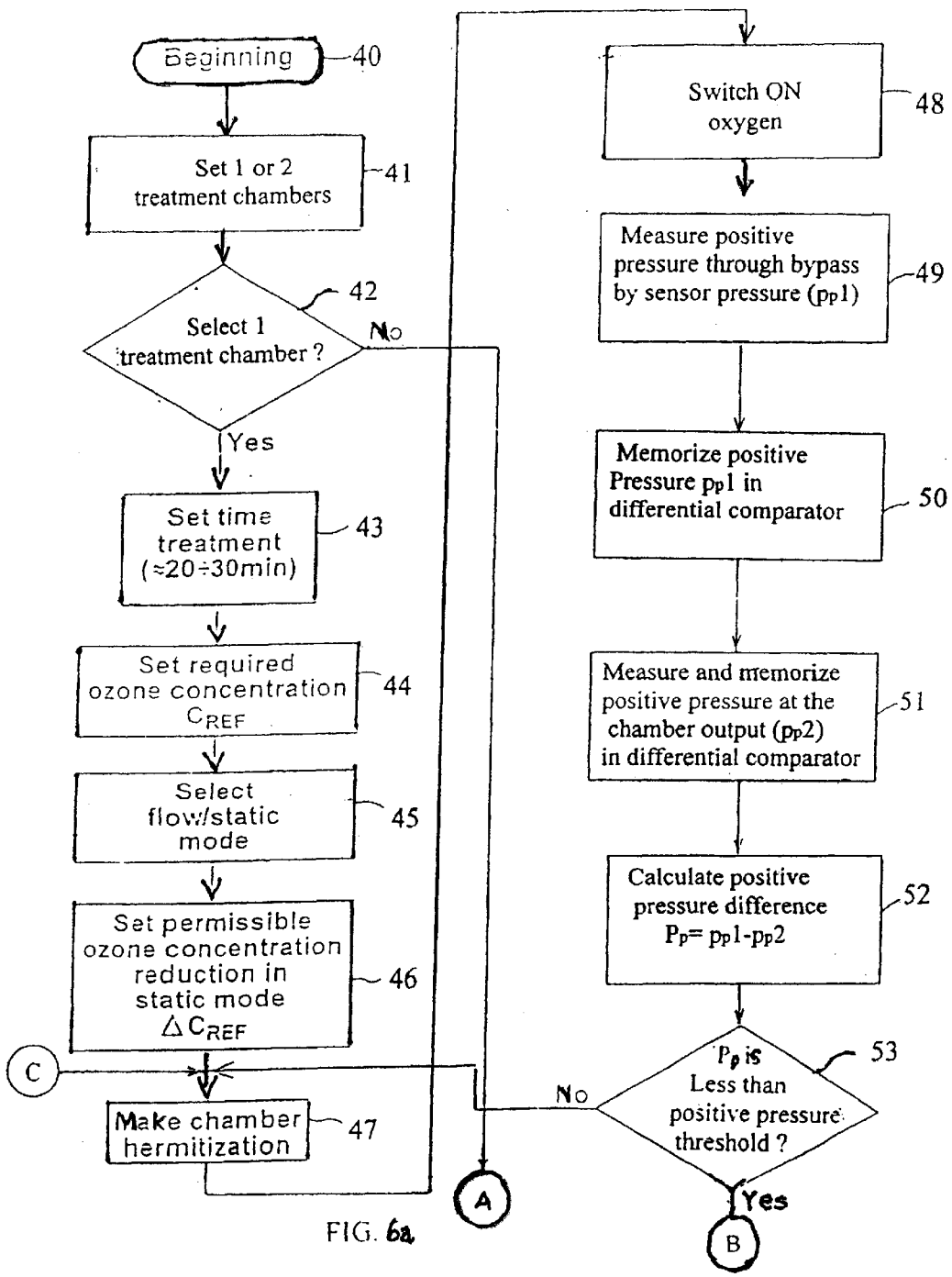
FIGS. 6A–6J illustrate a detailed flow chart describing a preferred mode of operation of the apparatus used for treating objects with ozone.
Figure 6B:
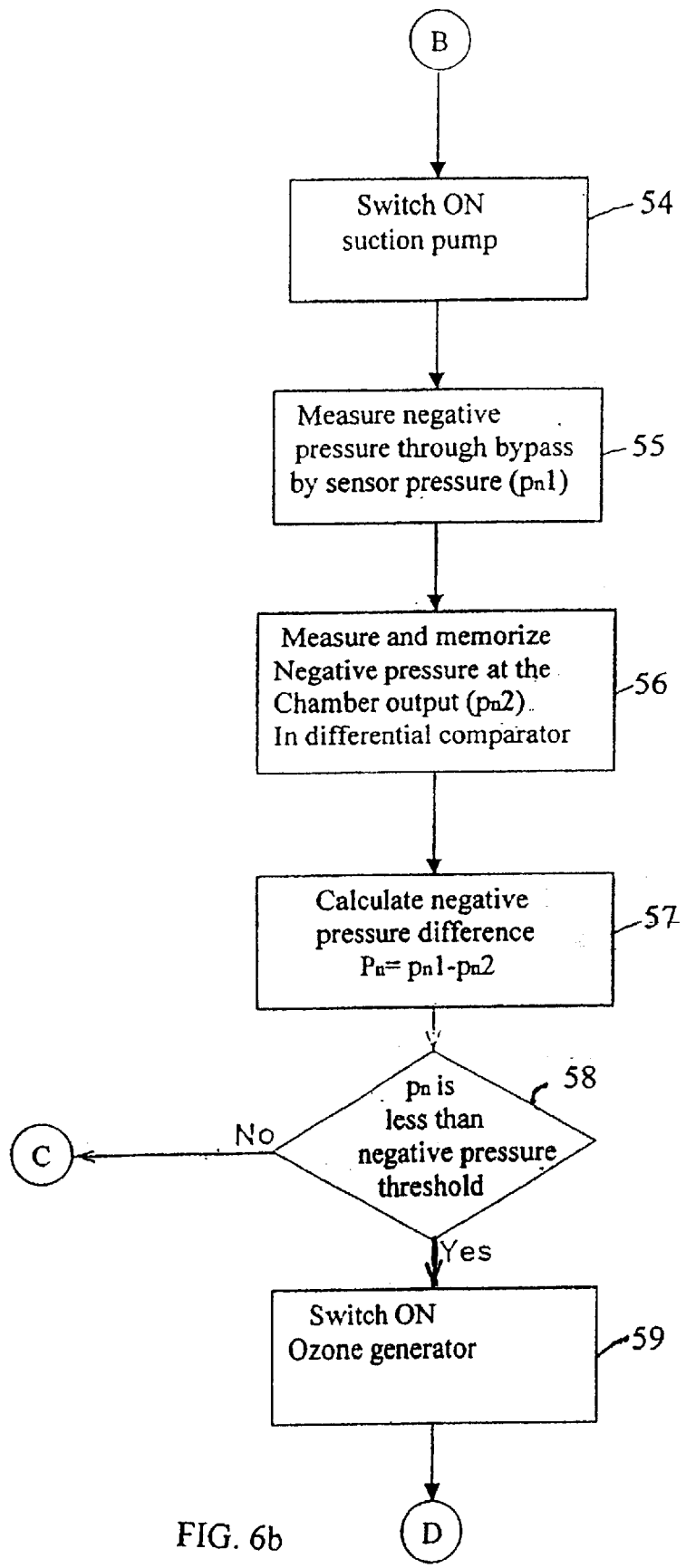
Figure 6C:
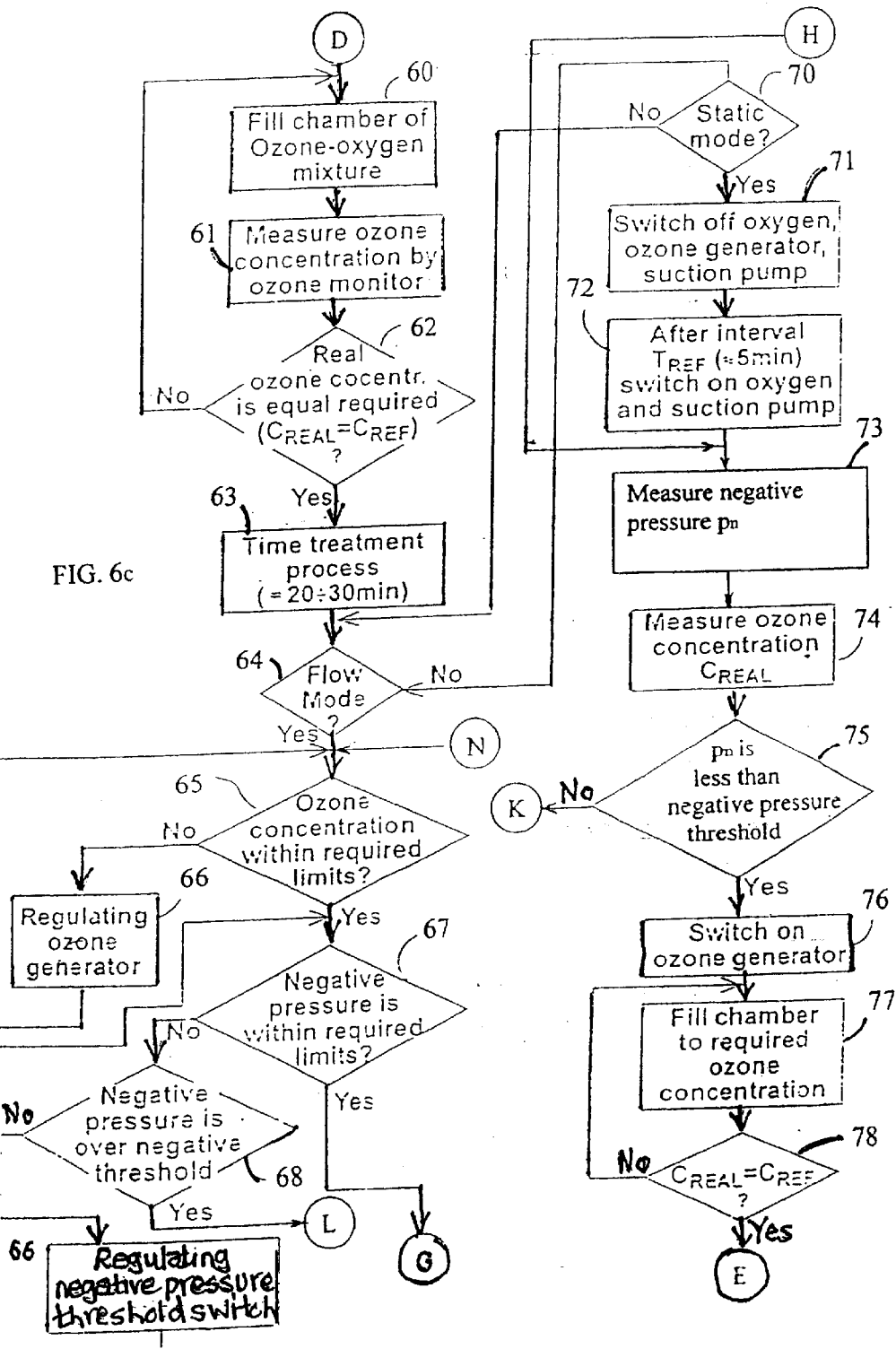
Figure 6D:
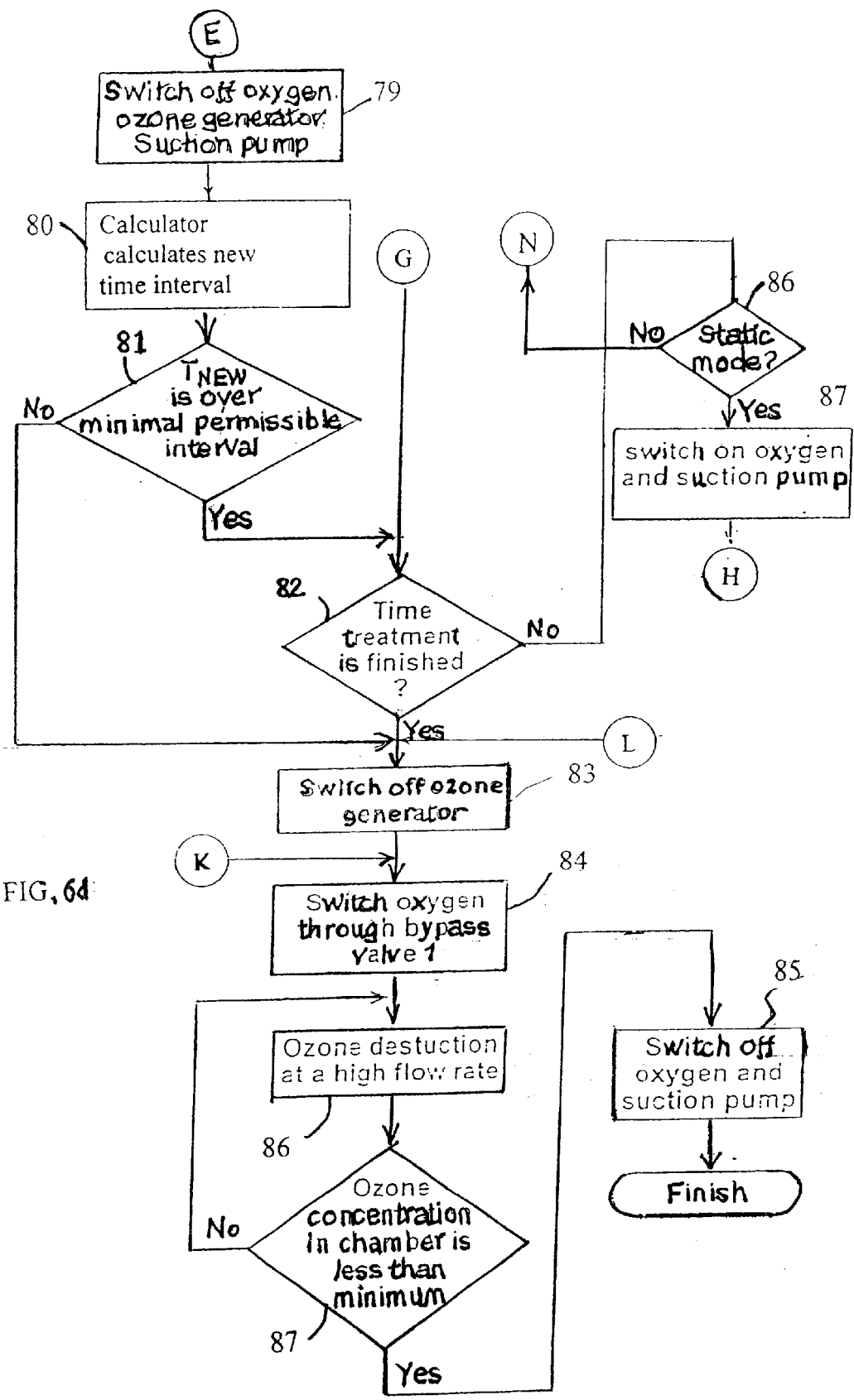
Figure 6E:
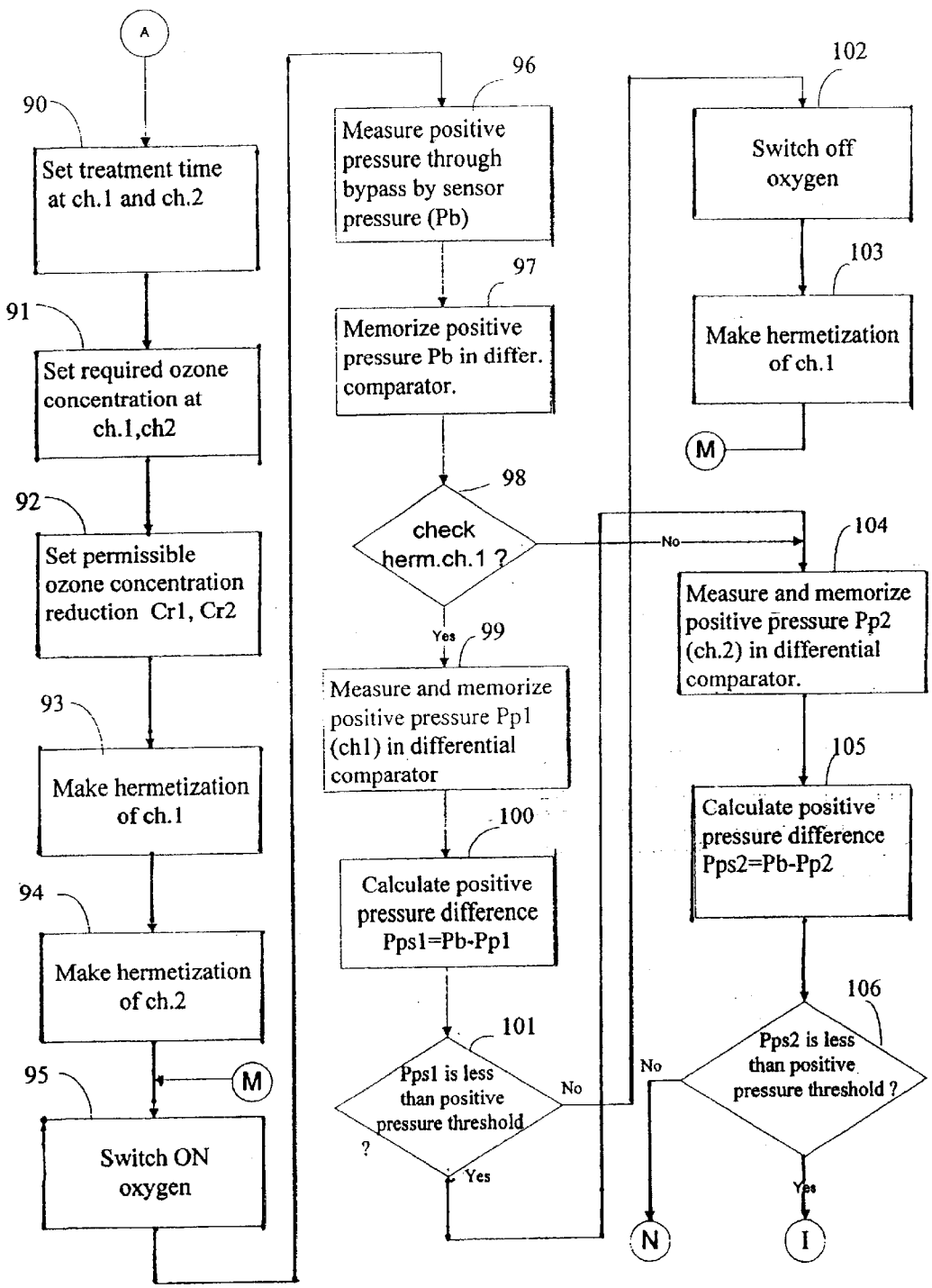
Figure 6F:
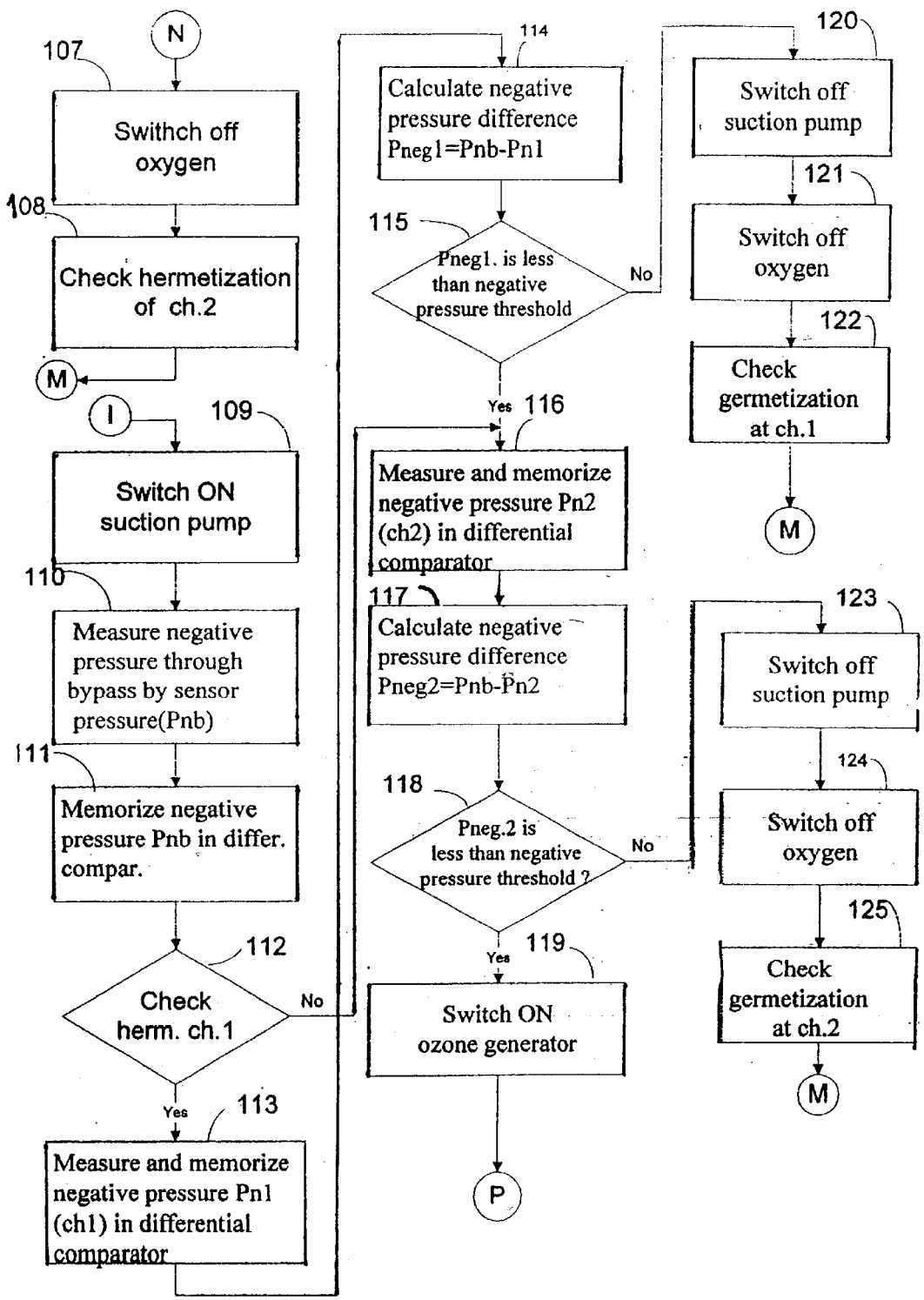
Figure 6G:
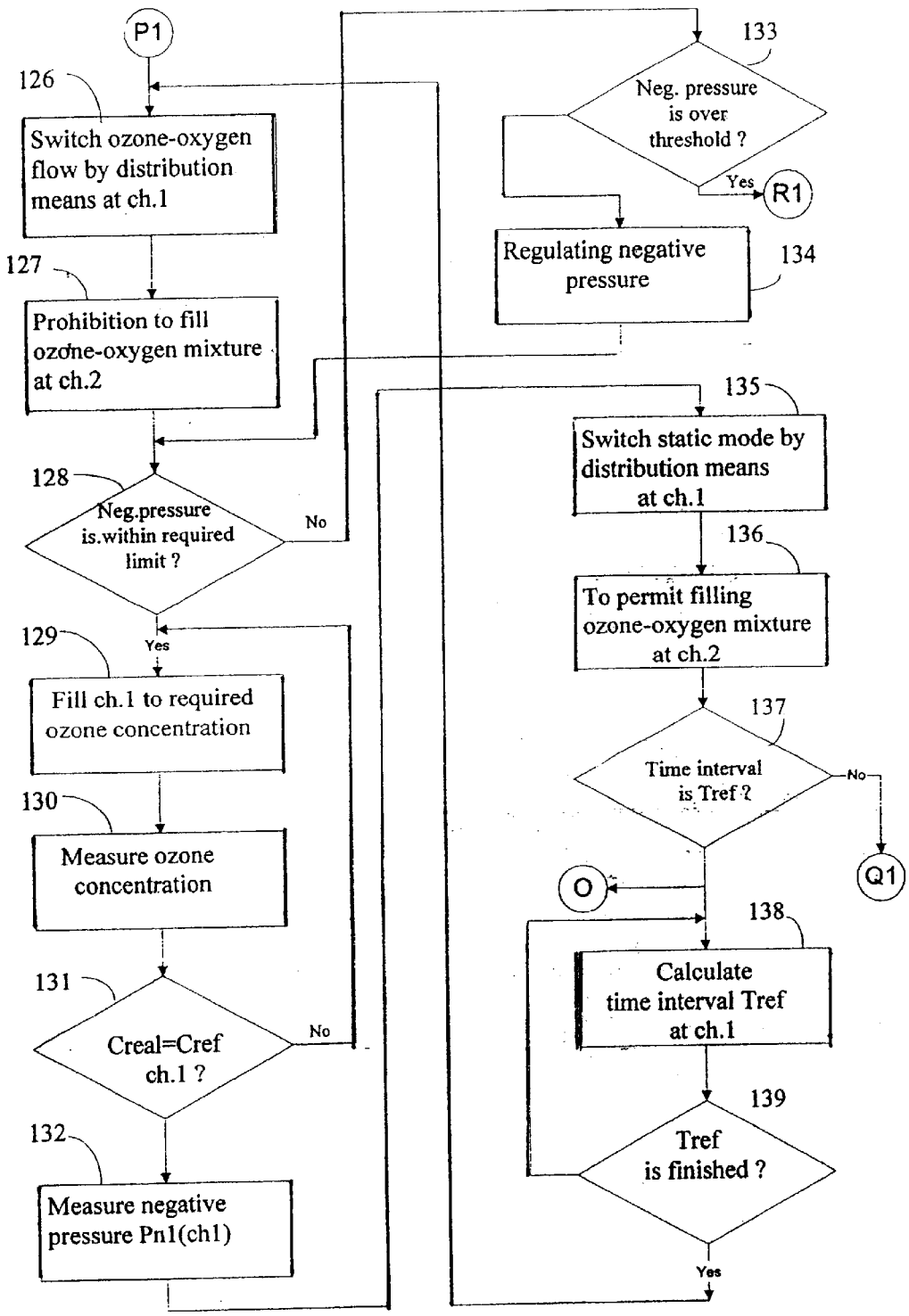
Figure 6H:
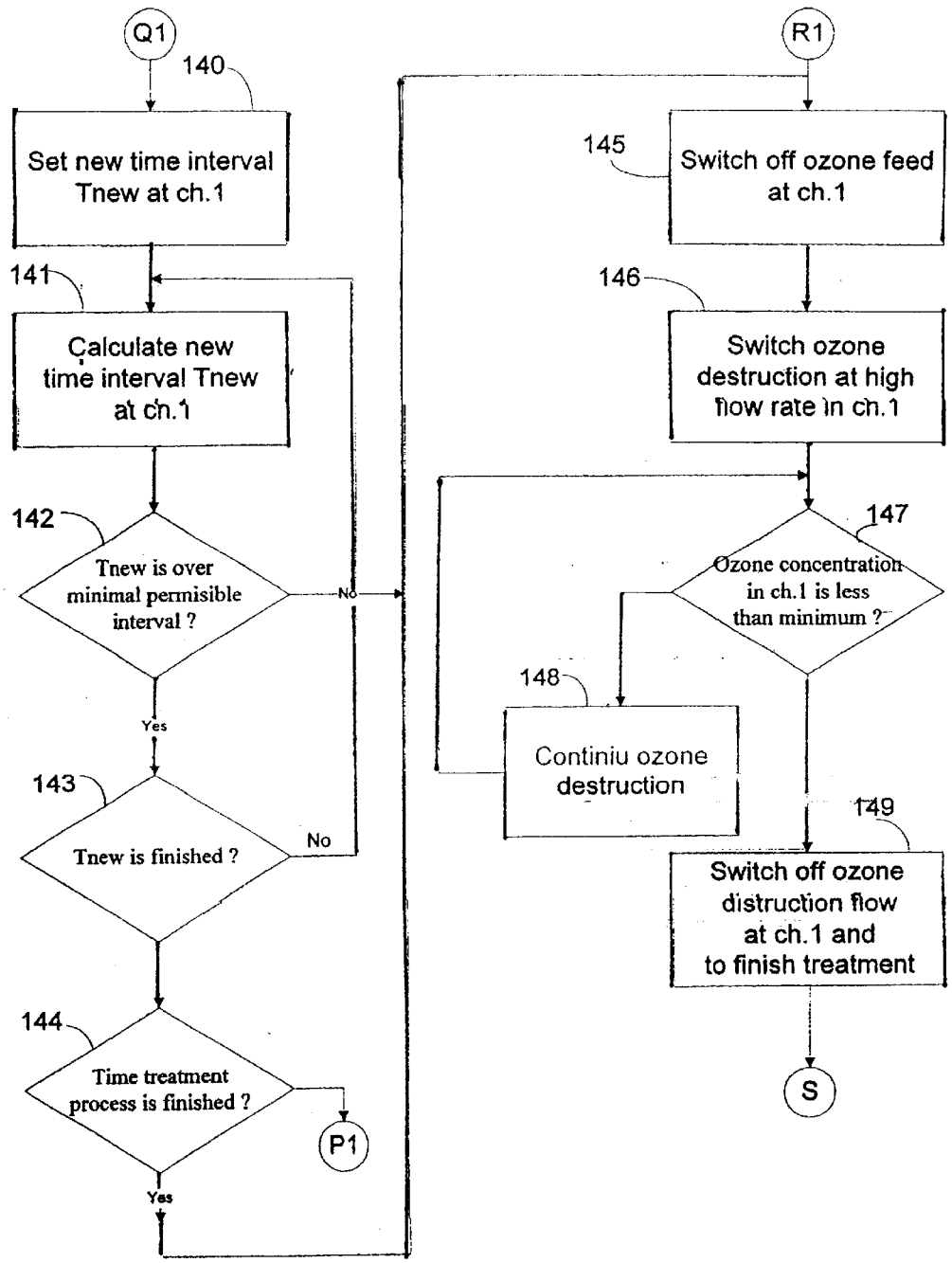
Figure 6I:
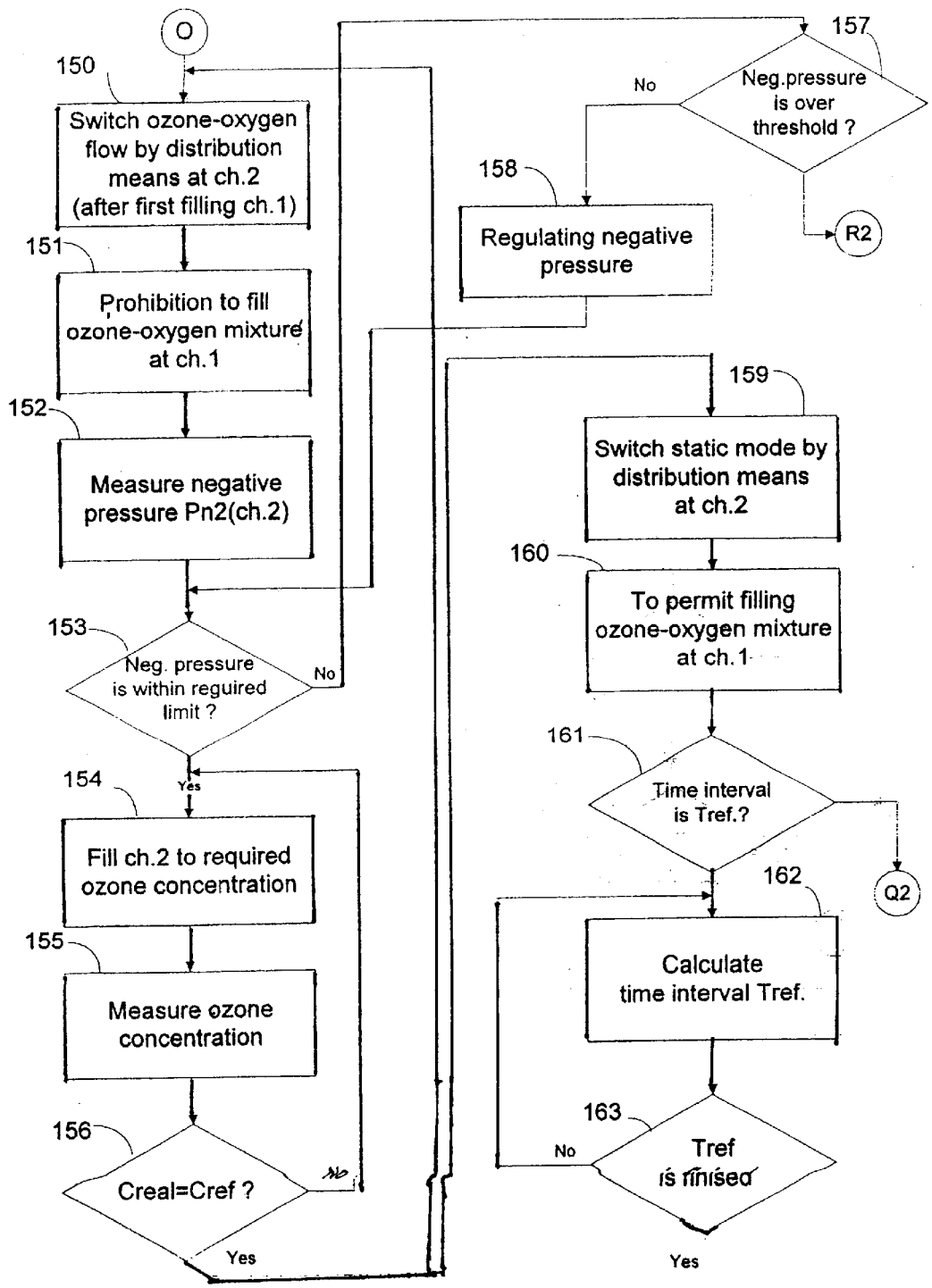
Figure 6J:
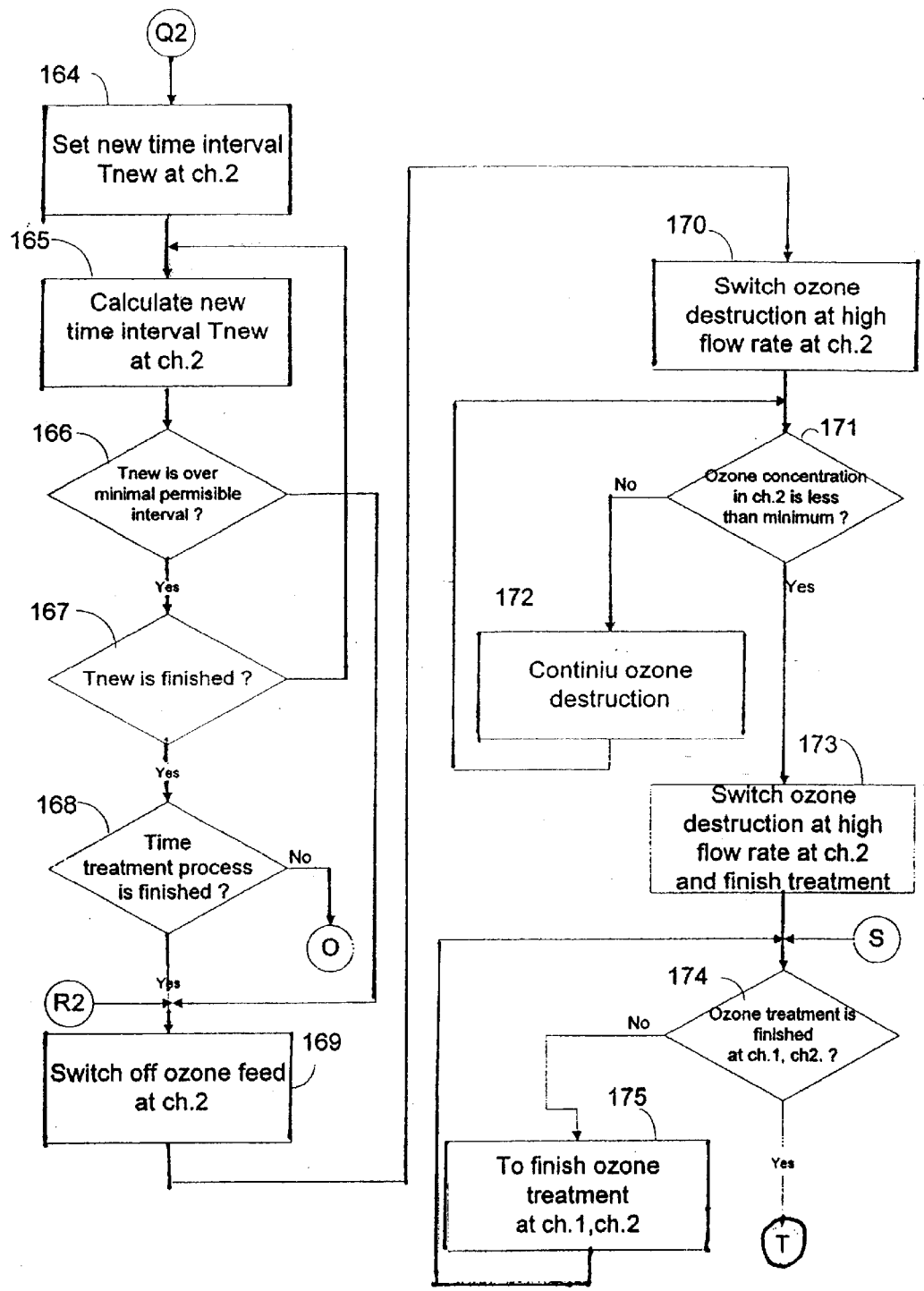

A detailed block diagram of the apparatus according to the present invention is shown in FIG. 4, and includes the supply of ozone-oxygen mixture, the distributing means, the ozone monitor, the ozone destruct or, the suction pump, and the control system.

The supply of the ozone-oxygen mixture to the treatment chamber 3 is shown in FIG. 4. It includes a container of compressed oxygen 14 connected, via a valve 15 and a flow meter 17 to an ozone generator 18. The ozone generator 18, which may be of a known construction, is connected by a connecting line 19 to a first commutator.

The ozone supply illustrated in FIG. 4 further includes a bypass line 16 from valve 15 to the outlet end of the ozone generator 18 for bypassing the ozone generator. A distributing means is intended to deliver an ozone-oxygen mixture of a predetermined concentration to the treatment chamber 3 and to produce by-pass of all chambers. The distributing means includes a first commutator 20 to switch inlets 4 of the treatment chamber 3, a second commutator 22 to switch outlets 5 and 11 of the treatment chamber and bypass line 21 from the first commutator 20 to the second commutator 22 thereby bypassing the treatment chamber 3.

The ozone monitor 25 is connected via a commutator 22 to outlets 5 of treatment chamber 3 to measure the ozone concentration within chamber 3. The ozone destruct or 26 is connected between the outlet of ozone monitor 25 and the inlet of suction pump 27 to bring about the destruction of ozone, outgoing from chamber 3 and to prevent suction pump 27 from ozone action. Suction pump 27 produces negative pressure within treatment chamber 3.

The control system includes sealing check means 28, treatment chamber selector 31, controller 32, input data unit 33, and output data unit 37. Controller 32 provides control of oxygen container 14, ozone generator 18, valve 15, first commutator 20, second commutator 22, and suction pump 27.

Bypass line 16 and control valve 15 permit controller 32 to cause only pure oxygen, or an ozone/oxygen mixture of the required concentration, to be delivered to the treatment chamber 3. Bypass line 21 and controlled commutators 20 and 22 permit controller 32 to measure the pressure drop within chamber 3. This is done by first operating commutators 20 and 22 to direct all the flow through the bypass 21 to the outlet end of chambers 3, and then operating commutators 20 and 22, to direct all the flow through one and then other chamber 3. These two operations enable measurements to be made of the pressure drop through each chamber 3. The sealing check means includes a differential pressure sensor 30 to measure pressure within treatment chamber 3 both over atmospheric (positive) and lower than atmospheric (negative) pressure, a pressure memory differential comparator 29, to calculate a pressure difference of oxygen flow at the inlet and at the outlet of treatment chamber 3 (pressure drop), at first, for positive pressure and, then, for negative pressure before beginning of ozone treatment. Only, if both positive pressure drop and negative pressure drop of oxygen flow through the treatment chambers 3 are in required limits, then the controller 32 switches on the ozone generator 18 and permits to deliver ozone to treatment chambers 3. The controller 32 also is programmed to maintain a predetermined negative pressure during filling of the treatment chambers with ozone. The controller 32 receives electrical signal from sensor 30, corresponding to real negative pressure within treatment chamber 3, and it controls the suction pump 27 to change it's rate for maintaining the required negative pressure. Therefore, sealing check means 28 together with controller 32, check the quality of the sealing of the treatment chamber 3 and prevent ozone leakage from treatment chamber 3 to the atmosphere.

The treatment chamber 3 is filled with ozone until the predetermined ozone concentration is established. The ozone concentration at the outlet of the treatment chamber 3 is continuously monitored by ozone monitor 25 which supplies feedback signals to controller 32 for controlling the ozone generator 18. Controller 32 compares the actual ozone concentration (Creal) as detected by the ozone monitor 25 with a reference concentration (Cref) and controls the ozone generation 18. Controller 32 produces the ozone reference for each treatment chamber itself on basis of data received from an input data unit 33.

The input data unit 33 comprises a patient number unit 34 to determine the index number of the patient to be treated, a wound status unit 35 to determine a quantity of granulation of the wound, and a bacteriological data unit 36 to determine a bacteria quantity to be measured before ozone treatment. According to the obtained data from units 34, 35 and 36 regarding the state of the object to be treated before ozone treatment, the controller 32 regulates the ozone concentration and time of the treatment.

The illustrated apparatus is operated only in the Static operational mode after filling of the treatment chamber with the ozone-oxygen mixture. In such a mode, there is no flow into or out of the treatment chamber 3 after filling of the treatment chamber with the ozone-oxygen mixture. A normal treatment is generally for a period of 15—30 minutes. Since ozone is relatively unstable, the concentration of the ozone within the treatment chamber continuously diminishes during this treatment period. The rate of diminution is not easily predetermined since it depends upon many factors, including temperature and humidity conditions among others.

Ozone treatment for healing wounds is generally optimum when the ozone concentration is between 2—5% of the ozone/oxygen mixture. Thus, if the treatment starts out with a 5% ozone concentration, during the course of the treatment the concentration could diminish so as to substantially reduce the effectiveness of the treatment. Since there is no flow in the Static operational mode, the ozone concentration cannot be detected by the ozone monitor 25 unless a flow is produced through the outlet of the treatment chamber 3. Controller 32 determines the short testing periods where flow is produced through treatment chamber 3 and during intervals between the test periods. This flow is tested for any drop in ozone content. Controller 32 controls ozone generator 18 and distributing means to introduce into the treatment chamber 3 a quantity of fresh ozone to make-up for any drop of ozone content therein. The controller 32 also employs the magnitude of the make-up quantity to determine the time interval to the next testing period according permissible drop concentration. Thus, if only a small make-up quantity of ozone is needed to restore the optimum concentration, the time interval to next testing period will be longer than if a large make-up quantity of ozone is required. During the test periods controller 32 controls the suction pump 27 to produce a negative pressure within treatment chamber 3.

The control system comprises an output data unit 37, which compiles all data about the object being treated in the form of an index number which includes quantity of ozone sessions, and other parameters of each session.

The control system includes a Selector of treatment chamber 31 which selects the number of treatment chambers 3 which can be used for ozone treatment. Use of some treatment chambers for ozone treatment for some objects simultaneously is possible only in the Static mode operation. Simultaneous operation of two chambers is shown in FIG. 5.

FIG. 5 illustrates: t1-check sealing of treatment chamber 3-1; t2-check sealing of treatment chamber 3-2; t3-filling of chamber 3-1 with ozone-oxygen mixture; t4-filling of chamber 3-2 with ozone-oxygen mixture; t5-initial time interval for chamber 3-1; t6-initial time interval for chamber 3-2; t5, t9, t13-testing periods and t7, t11, t15-time intervals for chamber 3-17; t8, t12, t16-testing periods and t10, t14-time intervals for chamber 3-2; t17 destruction for chamber 3-1 t18-destruction for chamber 3-2. Controller 32 controls the commutators 20 and 22 to produce testing periods in turn to reach treatment Chamber 3. Thus, if the testing period is in one chamber, there will be time intervals in the other chambers.

In the Static mode, the basic time interval is where there is no ozone flow into or out of the treatment chamber 3. In the absence of the flow it is impossible to produce a negative pressure within treatment chamber 3 to prevent an ozone leakage to the atmosphere. In this case accidental exhaust of ozone leakage from the treatment chamber 3 is possible. This is especially important if several treatment chambers operate simultaneously.

FIG. 6 illustrates an embodiment of the treatment chamber 3 with additional protection from ozone leakage. In addition to the treatment chamber shown in FIG. 3, the new treatment chamber comprises an outer rigid ring 10 (part of the housing 2) with a second outlet 11 and a second flexible sleeve 12. One end of the second flexible sleeve 12 is connected to the object higher than the first flexible sleeve 9, and its other end is connected to the outer rigid ring 10. The outer rigid ring has a groove 13 on its outer surface for connection with sleeve 12. This connection may be made for example, by a rubber elastic ring (not shown). Connection of the second sleeve 12 both with object F and with the outer ring 10 is non-hermetic. Outlet 11 is connected through commutator 22 to the second outlet of the suction pump 27. Suction pump 27 removes any accidental exhaust of ozone leakage from treatment chamber 3, during time intervals in the Static mode operation.

5.2 Wounds and Skin Lesions 5.2.1 The Diabetic Foot

From 50–70% of all nontraumatic amputations in the United States is in the diabetics (A Report of the National Diabetes Board:NIH Publication 81-2284, 1980, p25). The breakdown of the foot in the diabetic is commonly due to a combination of neuropathy and infection, with or without some vascular impairment. If an ingrown toenail or ulcer occurs and remains untreated because of lack of pain sensation, the infection may spread throughout the foot, creating a gross infection that demands more blood supply than the impaired vessels can provide. The resulting gangrene may demand an amputation. Physicians sometimes get the impression that trophic ulcers in diabetics occur without loss of sensation. They are then surprised when breakdown occurs. The problem is that a foot may be vulnerable to damage long before gross sensory loss is noted. The therapeutic compositions of the present invention are designed to prevent the breakdown and to treat the ulcers associated with diabetics.

5.2.2 Pressure Ulcers

Pressure ulcers continue to be a major healthcare problem especially for the elderly patient with limited mobility. The risk of death among geriatric patients increases fourfold when a pressure ulcer develops and sixfold when a ulcer does not heal. Development of pressure ulcers has been recognized as a source of malpractice liability for all who provide patient care. Courts have shown little sympathy for healthcare providers who permit such wounds to occur or persist. In *West v. Van-Care, Inc.* (Case No. CV-91-617), an Alabama jury returned a verdict for $65 million when an elderly male developed a 10 inch, gangrenous pressure ulcer while residing at the defendant's nursing home. There is therefore a need not only for better devices (e.g. mattresses) to prevent the formation of sores, but also a therapeutic device or method that can be used in providing better skin care and accelerating the wound healing process in pressure ulcers.

5.2.3 Burns

Burns are a very common injury, with estimates of at least two million individuals per year being burned severely enough to require medical attention. The classic description of first-, second-, third-, and fourth-degree burns is an anatomic one based on the depth of injury related to the skin anatomy. A first-degree burn has not penetrated the basal layer of the epithelium. In essence, the epithelium has not been breached. These injuries are typified by sunburns and essentially need little care, except possibly for a moisturizer. A second-degree burn extends from beneath the basal layer of the epithelium to, but not through, the entire epidermis. Epithelial cells lining the dermal adnexa remain viable and migrate to cover the s ace of the wound. A third-degree bum extends completely beneath the dermis into the fat. A fourth-degree burn extends into muscle and bone and requires treatment in a specialized burn center. The therapeutic compositions of the present invention are suitable for accelerating wound healing in burn patients, in patients with inhalation injury, upper airways burns, lower airways burns or lung burns and in the management of related complications.

The process of wound healing includes an initial proliferative phase promoting rapid cell metabolism and proliferation, disposal of debris, mobilization of fibroblasts and restoration of circulation. It is during this period that the wound is most susceptible to infection. During the subsequent phase (also referred to as the fibroplastic phase) of wound healing, increasing tensile strength parallels the rise in collagen content of the wound. Thus, there has remained a need to develop compositions for wound healing such that they contain non-biodegradable microspheres and other extracellular components capable of promoting the proliferative phase and regulating the fibroplastic phase in situ.

Hence, there must be a balance between promotion of the proliferative phase and the onset of the fibroplastic phase during wound healing in animals and human beings for different conditions including, but not limited to, burned tissues, infections following surgery, surgery wound breakdown, internal ulcers, hemorrhage, bone gangrene, pressure sores, decubitis, compromised amputation sites, non-healing traumatic wounds, cosmetics, after shave, dental work, chronic ulcers (of the diabetics, varicose vein, post stroke), destruction of tissue by radiation, spinal injury wounds, gynecological wounds, chemical wounds, vessel disease wounds, diabetic skin sores, diabetic feet, physical trauma, post plastic surgery suture sites, sunburns or episiotomies.

5.3 Ozone Treatment for Immune Disorders

The present invention also provides a method of stimulating or activating the immune system in a human subject by subjecting about 1.0 ml to about 200 ml of blood from a human subject with an effective amount of ozone, followed by administration of the treated blood to a human subject. The device of the present invention is also used to treat an immune system disorder in a human subject by subjecting about 1.0 ml to about 200 ml of blood from a human subject with an effective amount of ozone, followed by administration of the treated blood to a human subject.

The useful and preferred ranges of ozone concentration, temperature and other conditions of these methods of treatment are similar to those as described for the treatment of various types of wounds and skin lesions on different parts of the body. The immune system disorders which may be treated by this method include inflammatory conditions, allergic conditions, autoimmune conditions, arthritis, rheumatoid arthritis, asthma, graft-versus host disease, diabetes mellitus, organ rejection, osteoarthritis, systemic lupus erythematosus, atopic allergy, multiple sclerosis, Reynaud's syndrome, allergic dermatitis, inflammatory bowel disease, psoriasis, sarcoidosis, a lymphoproliferative disorder or a neoplastic disorder.

The term "immune system disorder" is defined to mean the treatment of any disease that is associated with immunosuppression, or which may be benefited by increasing the activity of the immune system. Thus the application of ozone by the device of the present invention is also useful in the treatment of a variety of infectious diseases, for example, viral infections such as the HIV virus, hepatitis virus, tumors, or bacterial, yeast or protozoal infections.

In warm-blooded animals, there is a natural defense mechanism which produces in vitro naturally occurring free radicals in order to respond to antigens or other infectious pathogens. Phagocytic cells and lymphocytes give off superoxide which has an antimicrobial action. This antimicrobial action is attributed to superoxide, derivatives such as hydrogen peroxide, hydroxyl radical and the signlet oxygen. It is an object of the present invention to provide a method of treating microbe related infections wherein ozone is introduced into the body of a warm blooded animal which mimics or enhances the naturally occurring free radicals produced by the oxidative bursts in the cells in responding to such infections. There may be problems involved with over production or an excess of radicals with the cells of the host. Therefore the body has provided means for mediating or neutralizing these products once they have performed their antimicrobial functions. For example, the superoxide dismutase enzyme is effective in scavenging superoxide radicals in a simultaneous oxidation-reduction reaction with hydrogen called dismutation. Two superoxide radicals combine with two hydrogen atoms to form hydrogen peroxide and oxygen. Hydrogen peroxide is reduced by the enzymes catalase, glutathione peroxidase and myeloperoxidase into oxygen and water.

It is therefore an object of this invention to provide a device for treating antigenic related infections by the administration of ozone into the bloodstream of a warm blooded animal to enhance the ability of the body to utilize the free radicals as microbiocides.

Another object of this invention is to provide regulated amounts of ozone directly or in a physiological solution, in concentrations sufficient to bring about the desired disinfections, antimicrobial or decontamination properties when utilized for the desired in vitro or in vivo purposes. If necessary, the regulated application of ozone may be accompanied by administration of moderating and/or neutralizing amounts of antioxidants or reducing agents such as catalase, superoxide dismutase, myeloperoxidase or other suitable peroxidase, glutathione, glutathione peroxidase, ascorbic acid or other suitable agents. The moderating antioxidants and/or neutralizing agents may be administered just prior to, concurrent with or shortly following the administration of the regulated amount of ozone. The antioxidants or neutralizing agents may be administered either orally, intravenously or parenterally. In addition, the microbiocidal effects of ozone may be enhanced by the administration of effective amounts of enhancing microbiocidal agents. However, it is not necessary, or even desirable, to administer moderating agents due to the fact that the ozone dissipates rapidly into innocuous products and the dosage of ozone administered is sufficiently regulated to prevent unwarranted side effects and/or damage to tissues of the subject treated.

5.4 Ozone Treatment for Peripheral Vascular Disease

The present invention relates to a method of inhibiting platelet aggregation as well as to a method of therapeutically treating disease conditions associated with platelet aggregation, for example, peripheral vascular disease, thrombolic diseases such as coronary thrombosis and pulmonary thrombosis, stroke, eclampsia and pre-eclampsia, and hypertension. The method of the invention increases blood levels of prostacyclin, a substance which is known to inhibit platelet aggregation and relax peripheral blood vessels. The inventive method of treating blood with ozone has been unexpectedly found to increase blood levels of nitric oxide which may explain in part the effect of ozone on inhibiting platelet aggregation.

5.5 Chronic Venous Insufficiency

Chronic venous insufficiency in the leg is manifested by edema and dilated superficial veins. In atrophic blanche, the ischemia stems from the equalization of the pressure at the arteriolar and venular ends of the skin capillaries due to venous hypertension. The result is decreased pressure driving blood from the arteriolar end to the venous end of the capillary, with resultant sludging of platelets and clot formation. The use of judicious and standardized ozone dosages can elicit the formation of Reactive Oxygen Species (ROS) acting as natural physiological activators of several biological functions. Ozone appears to stimulate the phagocyte activity of neutrophils and to modify immunoglobulin levels. In response to an array of endogenous and exogenous factors, the activation of leucocytes is paralleled by an abrupt rise in oxygen consumption, a metabolic event termed the "respiratory burst" during which ROS are generated. These products kill infectious agents, which are then taken up by phagocytosis. ROS also clean wounds from necrotic areas. Ozone via ROS can induce the expression and release of several growth factors such as platelet derived growth factor (PDGF, transforming growth factor and others. These are the main cytokines that play a major role in stimulating particular facets of the healing process and the endogenous release of these cytokines is likely to accelerate wound healing. Advantages of ozone are proving about this grate potential for treatment of badly healing wounds.

6. EXAMPLES

Studies were performed in diabetic individuals to determine the effect of ozone treatment on wound healing. The first case study involved a diabetic human subject with an advanced wound in the foot.

FIG. 7A describes the wound before ozone treatment and FIG. 7B describes the same wound after 22 sessions of ozone treatment.

The second study involved a human subject who had a chronic venous ulcer wound on the side of the leg.

FIG. 8A describes the wound before ozone treatment. FIG. 8B describes the wound after forty nine (49) sessions of ozone treatment.

The third study involved a human subject who had a post-operation wound on the side of the leg.

FIG. 9A describes the wound before ozone treatment. FIG. 9B describes the wound after sixteen (16) sessions of ozone treatment.

The fourth study involved a human subject who suffered from a traumatic wound.

FIG. 10A describes the wound before ozone treatment, FIG. 10B describes the wound after twenty-six (26) sessions and FIG. 10C after skin graft treatment.

It is evident in all above three studies that ozone treatment markedly improves the healing of each of the wounds regardless of the stage of the wound. These studies indicate a theraputic role for ozone, applied under controlled conditions in the treatment of various types of wounds.

It will thus be seen that the objects set forth above, among those made apparent from the preceding description, are efficiently attained and, since certain changes may be made in carrying out the above method and in the compositions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall there between.

What is claimed is:

1. A device for the treatment of objects using an effective amount of ozone, the device comprising:

at least two sealed treatment chambers for objects to to be treated, wherein each treatment chamber is used for one object;

each treatment chamber being hermetically sealed by a sealing means to provide a complete seal;

each treatment chamber includes an inlet for introducing ozone-oxygen mixture therein and an outlet for removing the ozone-oxygen mixture therefrom;

a supply of ozone-oxygen connected to inlets of treatment chambers;

a suction pump connected to outlets of treatment chambers;

a distribution means for delivering the ozone-oxygen to each of the treatment chambers;

a control system for controlling the supply of ozone-oxygen mixture, the suction pump and the distribution means, the control system being designed to produce a static mode operation in all treatment chambers wherein is no ozone flow into or out of the treatment chambers except during testing periods when an ozone flow with a negative pressure is produced in one of the treatment chambers.

2. The device according to claim 1 wherein the supply of ozone-oxygen mixture includes a compressed oxygen container, a flowmeter, an ozone generator and a connecting line, the connecting line connecting the outlet of the ozone generator to the inlet of the distribution means, a first by-pass and a switch valve by passing the ozone generator and the flowmeter, and connecting the compressed oxygen container to the connecting line, wherein the switch valve is controlled by the control system.

3. The device according to claim 1, wherein the control system comprises a sealing check means and a controller;
wherein an input port the sealing check means is connected with an output port of the distribution means; and
an output ports of the sealing check means being connected to an input ports of the controller, thereby the sealing quality of each treatment chamber before delivering ozone or during ozone treatment.

4. The device according to claim 3, wherein the sealing check means comprises a differential pressure sensor to measure pressure within each treatment chamber.

5. The device according to claim 3, wherein the sealing check means further comprises a pressure memory differential comparator for recording the pressure difference in oxygen flow at the inlet and outlet of the treatment chamber both for positive and negative pressure before the beginning of ozone treatment.

6. The device according to claim 3, wherein the controller is programmed to set the static mode operation in each treatment chamber after filling said chamber with the ozone-oxygen mixture and to control the ozone concentration in each treatment chamber by means of the ozone generator.

7. The device according to claim 3, wherein the controller is programmed to produce at testing periods in turn for each treatment chamber; wherein the outflow at said testing period is tested for any drop in ozone content, and a quantity of fresh ozone is introduced into the treatment chamber to make-up for any drop of ozone content therein; thereby the controller controls the distributing means such that if a testing period is in one of the treatment chamber, there will be no ozone flow in any of the remaining treatment chambers.

8. The device according to claim 1, wherein the control system comprises a selector means for selecting the treatment chambers for ozone treatment.

9. The device according to claim 1, wherein the device comprises an ozone monitor connecting to the outlet of the distributing means.

10. The device according to claim 9, wherein the device further comprises an ozone destruct or connected to the outlet of the ozone monitor.

11. The device according to claim 1, wherein the device comprises an input data unit for entering the data of objects to be treated.

12. The device according to claim 11, wherein the input data unit comprises an unit for the patient number, a wound status unit and an unit of the bacteriological data.

13. The device according to claim 12, wherein the controller is programmed to determine a required ozone concentration and time of ozone treatment for each object to be treated according to the data entered into the controller from the input data unit.

14. The device according to claim 1, wherein the control system comprises an output data unit for recording the data on objects to be treated.

15. The device according to claim 1, wherein the each treatment chamber comprises:
an air-impermeable housing, said housing comprising a hollow construction to define a treatment chamber, said housing being formed with an inlet and an outlet for ozone, and with an opening for introducing into the treatment chamber an object to be treated;
a first flexible air-impermeable sleeve having one end lining the opening and its opposite end extending externally of the treatment chamber within the housing; and
a clamping ring clamping one end of the flexible sleeve to the housing.

16. The device according to claim 15, wherein the clamping ring is of conical configuration and is receivable with a friction fit over a complementary conical section of the housing circumscribing the opening therein, with one end of the flexible sleeve clamped between the conical ring and the conical section of the housing.

17. The device according to claim 16, wherein the sleeve of a flexible elastic material and its outer end firmly grips the object.

18. The device according to claim 15, wherein the flexible sleeve is of a pliable plastic material, and the device further includes a second clamping ring for clamping the outer end of the pliable plastic sleeve to the object.

19. The device according to claim 15, wherein the treatment chamber further comprises:
an outer rigid ring with a leakage outlet for removing any ozone leakage;
a second flexible sleeve having one end lining the opening, and an opposite end extending externally and non-hermetically with the outer rigid ring.

20. The device according claim 19, wherein the outer rigid ring has a groove in its outside surface, said groove being used for a non-sealing connection with the second flexible sleeve.

21. The method of treating at least two objects with ozone, wherein said objects are treated in the treatment chambers in a static mode in which there is no flow into or out of the chambers, except that when each test is performed at a testing periods in turn in each of the treatment chambers; an outflow is produced from the chamber, the outflow is tested for any drop in ozone content, and an equivalent quantity of fresh ozone being introduced into the chamber to maintain a constant ozone concentration therein.

22. The method according to claim 21, wherein the quantity of ozone in the treatment chamber is determined on the basis of the object treating status and the results of the bacteriological test.

23. The method of claim 21, wherein ozone is used to treat objects with diabetic ulcers.

24. The method of claim 21, wherein ozone is used to treat objects with burns.

25. The method of claim 21, wherein ozone is used to treat objects with traumatic wounds.

* * * * *